(12) United States Patent
Weissman et al.

(10) Patent No.: US 9,932,679 B2
(45) Date of Patent: Apr. 3, 2018

(54) ELECTROCHEMICAL CONVERSION OF HYDROCARBONS

(71) Applicant: ExxonMobil Chemical Patents Inc., Baytown, TX (US)

(72) Inventors: Walter Weissman, Basking Ridge, NJ (US); Sumathy Raman, Annandale, NJ (US); Mark A. Greaney, Upper Black Eddy, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 470 days.

(21) Appl. No.: 14/516,934

(22) Filed: Oct. 17, 2014

(65) Prior Publication Data

US 2015/0119542 A1  Apr. 30, 2015

Related U.S. Application Data

(60) Provisional application No. 61/898,066, filed on Oct. 31, 2013.

(30) Foreign Application Priority Data

Jan. 15, 2014  (EP) .................................... 14151211

(51) Int. Cl.
  *C25B 3/00*  (2006.01)
  *C25B 3/04*  (2006.01)
  (Continued)

(52) U.S. Cl.
  CPC .............. *C25B 3/04* (2013.01); *B01D 53/326* (2013.01); *C07C 2/06* (2013.01); *C07C 5/03* (2013.01);
  (Continued)

(58) Field of Classification Search
  CPC ........................................................ C25B 3/02
  (Continued)

(56) References Cited

U.S. PATENT DOCUMENTS 5,051,156 A * 9/1991 Scharifker ................ C25B 3/02
                                                     204/282
6,294,068 B1    9/2001 Petrovic et al.

FOREIGN PATENT DOCUMENTS

JP   S62240777   10/1987
WO   2004/034487   4/2004

OTHER PUBLICATIONS

Sundmacher et al., "Solid Electrolyte Membrane Reactors: Status and Trends," Catalysis Today (no month, 2005), vol. 104, pp. 185-199.*

(Continued)

*Primary Examiner* — Edna Wong

(57) ABSTRACT

An electrochemical conversion method for converting at least a portion of a first mixture comprising hydrocarbon to $C_{2+}$ unsaturates by repeatedly applying an electric potential difference, $V(\tau_1)$, to a first electrode of an electrochemical cell during a first time interval $\tau_1$; and reducing the electric potential difference, $V(\tau_1)$, to a second electric potential difference, $V(\tau_2)$, for a second time interval $\tau_2$, wherein $\tau_2 \leq \tau_1$. The method is beneficial, among other things, for reducing coke formation in the electrochemical production of $C_{2+}$ unsaturates in an electrochemical cell. Accordingly, a method of reducing coke formation in the electrochemical conversion of such mixtures and a method for electrochemically converting carbon to $C_{2+}$ unsaturates as well as an apparatus for such methods are also provided.

9 Claims, 8 Drawing Sheets

(51) Int. Cl.
| | |
|---|---|
| *C25B 15/02* | (2006.01) |
| *C07C 2/06* | (2006.01) |
| *C07C 5/03* | (2006.01) |
| *C07C 29/04* | (2006.01) |
| *C08F 2/00* | (2006.01) |
| *B01D 53/32* | (2006.01) |
| *C25B 3/02* | (2006.01) |
| *C25B 3/10* | (2006.01) |

(52) U.S. Cl.
CPC ............... *C07C 29/04* (2013.01); *C08F 2/00* (2013.01); *C25B 3/00* (2013.01); *C25B 3/02* (2013.01); *C25B 3/10* (2013.01); *C25B 15/02* (2013.01); *B01D 2257/7022* (2013.01)

(58) Field of Classification Search
USPC ........................................................ 205/462
See application file for complete search history.

(56) References Cited

OTHER PUBLICATIONS

Hamakawa et al., "Electrochemical Methane Coupling Using Protonic Conductors," J. Electrochem. Soc. (Feb. 1993), vol. 140, No. 2, pp. 459-462.*

T.V. Choudhary, E. Aksoylu, D.W. Goodman , "Non-oxidative Activation of Methane", Catalysis Reviews, 45, No. 1, pp. 151-203 (2003).

P-H. Chiang, D. Eng, and M. Stoukides, "Electrocatalytic Methane Dimerization with YB-Doped SrCeO3 Solid Electrolyte", J. Electrochem. Soc. 138, No. 6, L11-L12 (1991).

"Electrocatalytic Methane Coupling in the Absence of Oxygen on a High-Temperature proton-Conducting Electrolyte", Catalysis Letters, 8, pp. 61-66 (1991).

S.Hamakawa, T. Hibino and H. Iwahara, "Electrochemical Methane Coupling Using Protonic Conductors", J. Electrochem. Soc., No. 2, pp. 459-462 (1993).

Y.Feng, J.Luo and K.T. Chuang, Fuel, 86, pp. 123-128 (2007).

K.C.Szeto, S.Norsic, L.Hardou, E. Le Roux, S. Chakka, J. Thivolle-Cazat, A. Baudouin, C. Papaloannou, J.M. Basset and M. Taoufik, "Non-oxidative coupling of methane catalyzed by supported tungsten hydride onto alumina and silica-alumina in classical and H2 permeable membrane fixed-bed reactors", Chem. Comm. 46, pp. 3985-3987 (2010).

B.Lee, T. Hibino, "Efficient and selective formation of methanol from methane in a fuel cell-type reactor", J.Catalysis, 279(2011) 233-240.

Lunsford, "The Catalytic Oxidative Coupling of Methane," Angew. Chem. Int. Ed. Engl., 1995, vol. 34, pp. 970-980.

Hibino et al., "Oxidative Coupling of CH4 using alkali-metal ion conductors as a solid electrolyte," J. Chem. Soc., Faraday Trans., 1996, vol. 92, No. 13, pp. 2393-2396.

Garagounis et al., "Solid Electrolytes: Applications in Heterogeneous Catalysts and Chemical Cogeneration," Ind. Eng. Chem. Res., 2011, vol. 50, No. 2, pp. 431-472.

\* cited by examiner

ELECTROCHEMICAL CONVERSION OF HYDROCARBONS

CROSS REFERENCE TO RELATED APPLICATIONS

This application claims the benefit of priority to U.S. Provisional Application No. 61/898,066, filed Oct. 31, 2013, and EP 14151211.1 filed Jan. 15, 2014 the disclosures of which are fully incorporated herein by reference.

FIELD OF THE INVENTION

The invention relates to electrochemical conversion of hydrocarbon-containing feed streams. In particular, embodiments of the invention relate to electrochemical conversion of methane to higher hydrocarbons, particularly ethylene.

BACKGROUND OF THE INVENTION

Electrochemical conversion of methane to higher hydrocarbon molecules, e.g., $C_{2+}$ saturated hydrocarbons and $C_{2+}$ unsaturated hydrocarbons is known. For example, the electrochemical conversion of methane has been accomplished in an electrocatalytic cell comprising an anode chamber, a cathode chamber, the anode chamber being separated from the cathode chamber by a membrane which prevents the flow of atoms, molecules, and electrons between the anode and cathode chambers, but permits the flow of ions. See, e.g., Chiang, et al., J. Eletrochem. Soc. 138, 6, L11, 12 (1991) and Hasakawa, et al., J. Electrochem. Soc. 140, 2, 459-462 (1993). In a conventional electrochemical cell, the anode chamber contains an anode in diffusive and electrical contact with the membrane, and the cathode chamber contains a cathode in diffusive and electrical contact with the membrane. The anode and cathode can be electrically connected via an external circuit, and the cell can be operated in either constant electric current or constant voltage mode.

In such a cell, methane may be conveyed to the anode chamber where the catalyst activates the methane to form $CH_3$ fragments, a hydrogen ion ($H^+$), and a free electron ($e^-$). The hydrogen ions transit the membrane, and at the cathode produce a product comprising, e.g., molecular hydrogen in systems where oxygen is absent, utilizing the free electrons conducted from the anode to the cathode via the external circuit. In systems where oxygen is present, a product comprising water is produced at the cathode. In either case, the desired $C_{2+}$ unsaturates are conducted away from the anode chamber.

In addition to activating the methane, the anode can further oxidize the $CH_3$ fragments produced by the activation, resulting in the production of surface-bound $CH_2$ fragments, which can in turn be oxidized to CH fragments. The CH fragments can be further oxidized to form carbon. Such carbon formation on the anode is the dominant reaction, resulting in a relatively small amount of $C_{2+}$ hydrocarbon being produced by the cell.

Methods of increasing methane conversion to $C_{2+}$ hydrocarbon have been described. For example, the use of an inorganic membrane in the cell enables the use of relatively high temperatures, thereby shifting equilibrium toward the formation of ethylene. The increase in ethylene, however, is accompanied by a loss in overall cell efficiency and an increase in carbon accumulation on the anode.

It is desired to increase the relative amount of $C_{2+}$ hydrocarbon produced at the cell's anode, and in particular the relative amount of ethylene, while maintaining cell efficiency and lessening the amount of carbon accumulating on the cell's anode.

SUMMARY OF THE INVENTION

It has been observed that the electrode's active sites for electrocatalytic conversion of $C_{1+}$ hydrocarbon (e.g., $C_{1+}$ alkane, such as methane) to $C_{2+}$ unsaturates are the same sites that are active for successive hydrocarbon oxidation. Successive hydrocarbon oxidation can lead to undesirable carbon formation on the electrode. It has been discovered that carbon formation can be mitigated, or even reversed, if the electric potential difference between the positive and negative electrodes of the cell is decreased, reversed in polarity, or even made substantially equal to zero for intervals during the conversion process. Further, in particular embodiments, the cell's operating conditions (e.g., electrode composition, voltage, current density etc.) are selected to favor the selection of C—C bond formation pathways over non-productive pathways.

Certain aspects of the invention provide an electrochemical conversion method carried out using an electrochemical cell. The electrochemical cell includes a first electrode, a second electrode, and at least one membrane located between the first and second electrodes. The process utilizes a first mixture as a feed to the cell's first electrode. The first mixture comprises hydrocarbon, e.g., methane. The first and second electrodes can be in physical contact with the membrane, and are generally located on opposite side of the membrane. The membrane can be one that is substantially non-porous, but allows for the flow of ions between the first and second electrodes. The process includes applying an electric potential to the cell to establish an electric potential difference, $V_1$, between the first and second electrodes (conventionally described as establishing an electric potential difference $V_1$ across the cell) during a first time interval $\tau_1$; and then changing the applied electric potential to establish a second electric potential difference, $V_2$ for a second time interval $\tau_2$. Generally, $\tau_2$ is less than or equal to $\tau_1$, e.g., $\tau_2$ can be in the range of from $0.01 \cdot \tau_1$ to $0.1 \cdot \tau_1$. Generally, $V_2$ is more negative (or less positive) than $V_1$. Optionally, $V_1$ and $V_2$ are related as follows: (i) $V_1 > 0$, $V_2 \geq 0$, and $V_2 = A_1 \cdot V_1$, where $A_1$ is in the range of from about 0.00 to about 0.99; (ii) $V_1 \geq 0$ and $V_2 < 0$; or (iii) $V_1 < 0$, $V_2 < 0$, and $|V_2| = A_2 |V_1|$, where $A_2 \geq 1.01$. Optionally, $V_1 \geq 0$, and $|V_2| < |V_1|$.

In operation, the cell produces a second mixture comprising $C_{2+}$ unsaturates in the vicinity of the second electrode during at least the second interval, and generally during the first and second interval. The second electric potential difference $V_2$ is typically selected so that $C_{2+}$ unsaturates can form from $CH_2$ fragments, but at a diminished rate of $CH_2$ oxidation to CH fragments and carbon compared to the rate at $V_1$.

After the second interval the applied electric potential can be changed again, e.g., to establish a third electric potential difference $V_3$ between the first and second electrodes for a third time interval $\tau_3$. Optionally, (i) $V_3$ is substantially the same as $V_1$ and/or (ii) $\tau_3$ is substantially the same as $\tau_1$. For example, $V_2$ can be more negative (or less positive) than $V_3$. Optionally, $V_3$ and $V_2$ are related as follows: (i) $V_3 > 0$, $V_2 \geq 0$, and $V_2 = A_3 \cdot V_3$, where $A_3$ is in the range of from about 0.00 to about 0.99; (ii) $V_3 \geq 0$ and $V_2 < 0$; or (iii) $V_3 < 0$, $V_2 < 0$, and $|V_2| = A_4 |V_3|$, where $A_4 \geq 1.01$. Optionally, $V_1 \geq 0$, and $|V_2| < |V_3|$.

After the third interval the applied electric potential can be changed again, e.g., to establish a fourth electric potential difference $V_4$ between the first and second electrodes for a third time interval $\tau_4$. Optionally, (i) $V_4$ is substantially the same as $V_2$ and/or (ii) $\tau_4$ is substantially the same as $\tau_2$. For example, generally $V_4$ is more negative or less positive than $V_3$. Optionally, $V_3$ and $V_4$ are related as follows: (i) $V_3>0$, $V_4 \geq 0$, and $V_4=A_5 \cdot V_3$, where $A_5$ is in the range of from about 0.00 to about 0.99; (ii) $V_3 \geq 0$ and $V_4<0$; or (iii) $V_3<0$, $V_4<0$, and $|V_4|=A_6|V_3|$, where $A_6 \geq 1.01$. Optionally, $V_3 \geq 0$, and $|V_4|<|V_3|$.

Optionally, the process is carried out continuously by conducting "n" changes in sequence to the applied electric potential to establish electric potential differences $V_n$ across the cell for a time interval $\tau_n$, where n is an integer $\geq 3$ corresponding to the number of times the applied electric potential is changed to produce the specified electric potential differences across the cell for the specified time interval. For example, the process can be carried out by (a) changing the applied voltage in sequence, e.g., by establishing a first electric potential difference $V_1$ across the cell for a first time interval $\tau_1$; (b) changing the applied electric potential to establish a second electric potential difference $V_2$ across the cell for a second time interval $\tau_2$, (c) changing the applied electric potential to re-establish the first electric potential difference $V_1$ across the cell for third time interval of duration $\tau_1$, and then (d) changing the applied electric potential to re-establish the second electric potential difference $V_2$ across the cell for a fourth time interval of duration $\tau_2$. The process can be operated continuously by repeating steps (a)-(d).

Other aspects of the invention provide a method for reducing coke formation in the electrochemical production of $C_{2+}$ unsaturates in an electrochemical cell comprising a first electrode, a second electrode, and at least one membrane situated between the first and second electrodes, the method comprising: (a) providing a first mixture to the first electrode, the first mixture comprising hydrocarbon, e.g., methane; (b) applying an electric potential to the cell to establish an electric potential difference, $V_1$, across the electrochemical cell sufficient to initiate the conversion of at least a portion of the hydrocarbon during a first time interval $\tau_1$; (c) establishing a second electric potential difference, $V_2$, across the cell for a second time interval $\tau_2$, wherein $\tau_2 \leq \tau_1$; repeating steps (b) and (c), and producing $C_{2+}$ unsaturates from the hydrocarbon in the vicinity of at least one of the first or second electrodes. The specified electric potential differences can be established by, e.g., one or more of: (i) changing the electric potential applied to the cell from a first applied electric potential to a second applied electric potential, (ii) by changing the composition and amounts of one or more feed components supplied to the cell, (iii) changing the composition and amounts of one or more product components conducted away from the cell, or (iv) changing one or more of the cell operating parameters such as one or more of the temperature and/or pressure at locations within the cell. $V_1$, $V_2$, $\tau_1$ and $\tau_2$ can have the same values as specified in any of the preceding aspects.

In other aspects, the invention provides a method for electrochemically converting carbon to $C_{2+}$ unsaturates comprising: (a) providing an electrochemical cell, the electrochemical cell having carbon deposited on the first electrode, a second electrode, and a membrane located between the first and second electrodes; (b) applying an electric potential to the cell to establish an electric potential difference across the cell during a first time interval $\tau_1$ sufficient for converting at least a portion of the deposited carbon to $C_{1+}$ hydrocarbon, such as methane; (c) changing the applied electric potential to establish a second electric potential difference, $V_2$, across the cell for a second time interval $\tau_2$ and producing $C_{2+}$ unsaturates from at least a portion of the $C_{1+}$ hydrocarbon produced in step (b); and (d) repeating steps (b) and (c). $V_1$, $V_2$, $\tau_1$ and $\tau_2$ can have the same values as specified in the preceding embodiments. Optionally, (i) at least a portion of the deposited carbon is graphitic carbon formed by the oxidation of hydrocarbon (such as methane) proximate to the first electrode and/or (ii) at least a portion of the $C_{2+}$ unsaturates produced during step (c) are formed from hydrocarbon produced during step (b).

Other aspects concern an apparatus for the electrochemical production of $C_{2+}$ unsaturates comprising: (a) an electrochemical cell comprising: (i) a first electrode chamber comprising first electrode, said first electrode chamber configured to receive a first mixture comprising $\geq 1.0$ wt. % of at least one hydrocarbon based on the weight of the first mixture; (ii) a second electrode chamber comprising a second electrode, said second electrode chamber configured to receive an oxygen-containing mixture comprising $\geq 10.0$ wt. % of at least one oxidant, based on the weight of the oxygen-containing mixture; and (iii) a membrane configured to locate between the first and second electrode, the membrane being substantially non-porous, but that is open to ion transport between the first and second electrodes; (b) means for applying an electric potential to the cell, e.g., a battery or a power supply in electrical communication with the electrochemical cell; and (c) means for regulating the electric potential applied to the cell, e.g., a voltage regulator configured to establish a first electric potential difference across the cell, $V_1$, for a first time interval $\tau_1$ and a second electric potential difference across the cell, $V_2$, for a second time interval $\tau_2$. $V_1$, $V_2$, $\tau_1$ and $\tau_2$ can have the same values as specified in the preceding embodiments. The apparatus can be utilized for carrying out any of the processes described in connection with the preceding aspects. Optionally, the hydrocarbon comprises methane. Optionally, the oxygen containing mixture comprises oxidant such as molecular oxygen.

DETAILED DESCRIPTION OF THE INVENTION

It has been observed that the successive oxidation of $C_{1+}$ hydrocarbon (such as methane) to carbon at an electrochemical cell's electrode, typically the anode, results from establishing an electrochemical potential $V_1$ across the cell for a time $\geq \tau_c$. Thus, it is observed that in the electrocatalytic conversion of hydrocarbon such as methane, when the cell is operated for a time, $\tau_{min}$, that is less than $\tau_c$ (e.g., $\tau \leq 0.1 \cdot \tau_c$, or $\tau \leq 0.01 \cdot \tau_c$), there is insufficient time to successively oxidize the methane to carbon (e.g., coke) on the cell's electrode. Consequently, if the electric potential difference between the positive and negative electrodes of the cell is decreased, reversed in polarity, or even made substantially equal to zero, $C_{2+}$ unsaturates such as ethylene can preferentially form in the cell's electrode chamber from $CH_2$ fragments. Since at least a portion of the $CH_2$ fragments have been consumed, fewer of these fragments remain at the electrode for oxidation to CH, and thereafter to carbon, as might occur when the initial electric potential difference is restored. In other words, changing the electric potential difference applied to the cell to produce a change in the electric potential difference across the cell for a time interval during the conversion lessens the successive oxidation of methane molecules to carbon atoms and allows the interaction of the $CH_2$ fragments to form the desired $C_{2+}$ unsaturates. This can be accomplished by (i) lessening an externally applied voltage, such as by decreasing an external voltage applied to the cell's negative electrode thereby making the voltage at the cell's negative electrode less positive with respect to the voltage at the cell's positive electrode and/or (ii) changing the one or more chemical components of the anode and/or cathode chamber.

Figure 2:
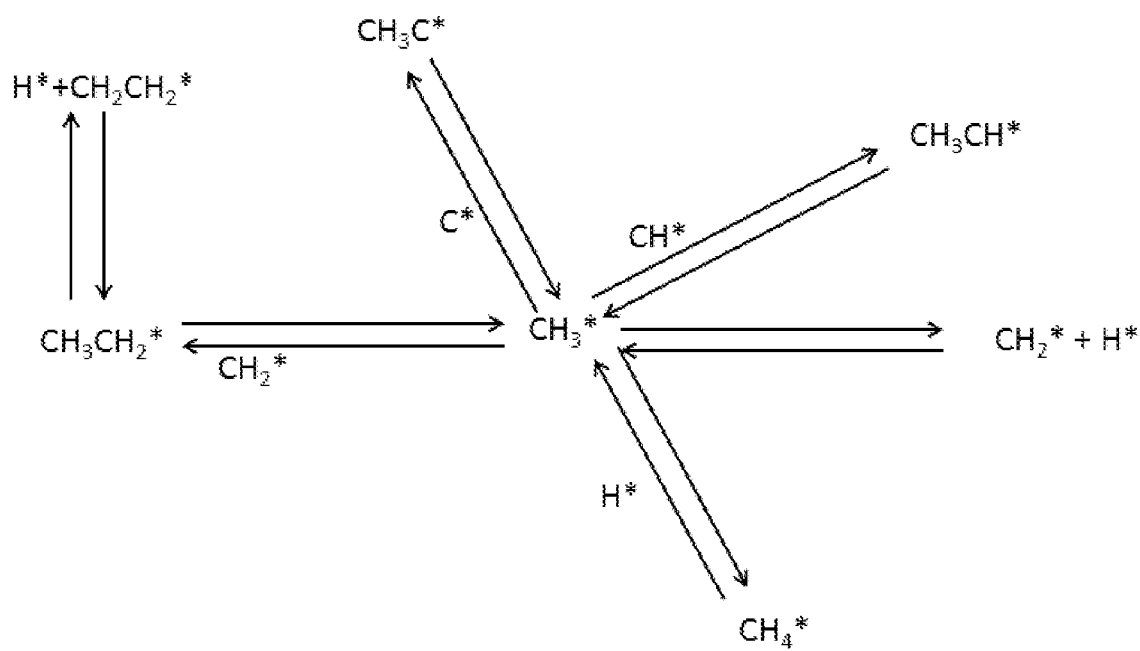
FIG. 2 schematically illustrates the competing reactions of various species in the electrocatalytic conversion of surface bound $CH_3$ fragments.
Figure 3:
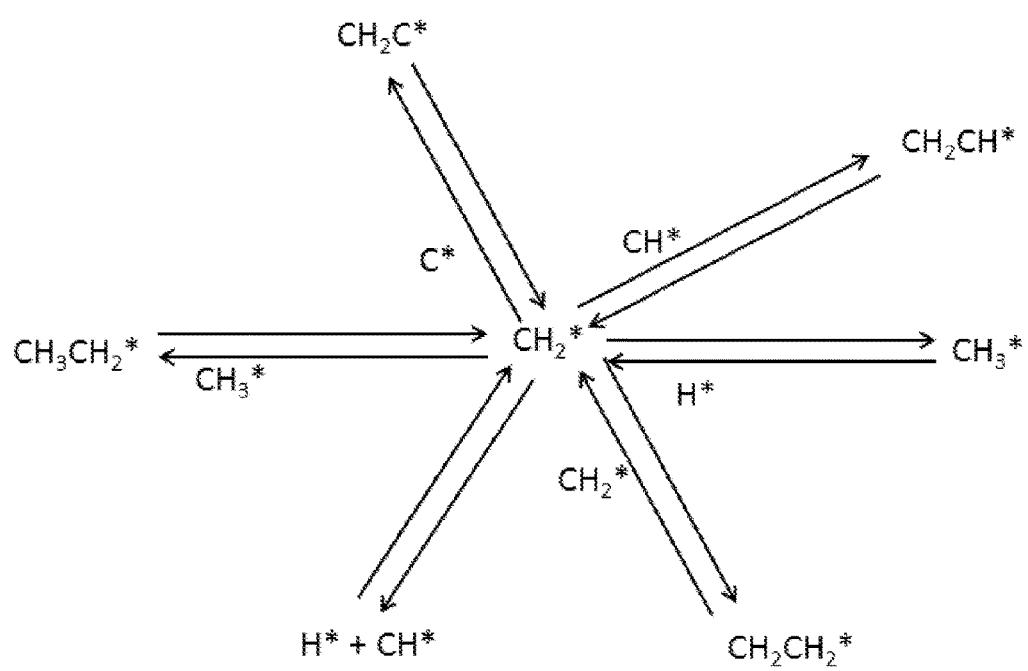
FIG. 3 schematically illustrates the competing reactions of various species in the electrocatalytic conversion of surface bound $CH_2$ fragments.
Figure 4:
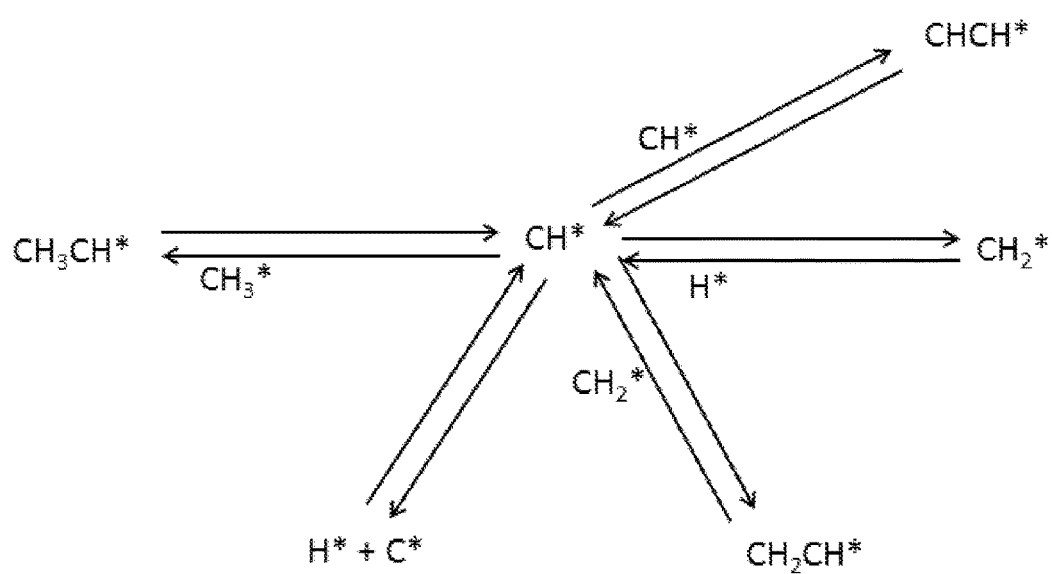
FIG. 4 schematically illustrates the competing reactions of various species in the electrocatalytic conversion of surface bound CH fragments.

The formation of desirable $C_{2+}$ unsaturates can be increased by selecting operating conditions that avoid other undesirable reactions shown in FIGS. 2-4. FIG. 2 illustrates the competing reaction pathways in the formation of various derivatives of $CH_3$ fragments on the electrode surface, where an asterisk indicates a surface-bound moiety. As FIG. 2 shows, once the $CH_3$ fragment forms, C—C formation is only one of many options for its continued reaction. One such option is the formation of $CH_2$ bound species, which can further react along one or more pathways, as FIG. 3 shows. As in the case of surface-bound $CH_3$ species, C—C bond formation may be more probable than with other pathways in the presence of $CH_2$, $CH_3$ and H fragments. It is believed that once the surface-bound CH fragment forms, the further oxidation to carbon depicted in FIG. 4 is highly favored on most electrode surfaces. It has been observed that mitigating CH fragment formation impedes the successive oxidation process and mitigates coke formation on the electrode.

The invention is applicable even in embodiments where an undesirable amount of CH fragmentation occurs, leading to carbon forming on at least one of the cell's electrodes. It has been observed that carbon on an electrode can be upgraded, i.e., converted to hydrocarbons including $C_{2+}$ unsaturates by establishing a sufficient electric potential difference, e.g., $V_1$, particularly in the absence of more reactive carbon-sources e.g., methane. Accordingly, in certain embodiments the flow of methane to the cell is lessened or halted when an electric potential difference $V_1$ is established across the cell.

Certain aspects of the invention will be described where the electric potential difference across the cell (or the current flowing through the cell) are established by applying a first electric potential to the cell during a first interval of duration $\tau_1$ and applying a second electric potential to the cell during a second interval $\tau_2$. The invention is not limited to these aspects, and this description is not meant to foreclose other aspects within the broader scope of the invention, such as those where the first and/or second electric potential difference across the cell are established by one or more of: (i) changing the composition and amounts of one or more feed components supplied to the cell, (ii) changing the composition and amounts of one or more product components conducted away from the cell, and/or (iii) changing one or more of the cell operating parameters, such as one or more of the temperature and/or pressure at locations within the cell (e.g., at one or more of the anode, cathode, membrane, anode chamber, cathode chamber, cell walls, etc.).

Certain aspects of the invention relate to an electrochemical conversion process. The process comprises providing an electrochemical cell comprising first electrode, a second electrode, and a membrane. The membrane, which is typically non-porous, is situated between the first and second electrodes. In the process, a first mixture comprising hydrocarbon, e.g., methane, is provided to the first electrode of the electrochemical cell. An electric potential is applied to the cell to establish an electric potential difference, $V_1$, across the electrochemical cell during a first time interval $\tau_1$. This produces carbon on the cell's first electrode at an average rate of $R_1$ (moles per second) during the first time interval. Next, the applied electric potential is changed to establish a second electrochemical difference, $V_2$, across the electrochemical cell for a second time interval $\tau_2$. This produces carbon on the first electrode at a rate $R_2$ during the second time interval. This also produces a second mixture comprising $C_{2+}$ unsaturates. In these aspects of the invention $R_2 < R_1$ and, preferably, $R_2 = B \cdot R_1$, where B is $\leq 1.0$, e.g., in the range of from about 0.01 to about 0.99, such as 0.1 to about 0.5. $V_1$, $V_2$, $\tau_1$ and $\tau_2$ can have, e.g., the same values as specified in any of the preceding aspects. Optionally, the $C_{2+}$ unsaturates are produced during the first time interval.

The first mixture comprises hydrocarbon, e.g., $\geq 1.0$ wt. % of $C_{1+}$ hydrocarbon, based on the weight of the first mixture, such as $\geq 25.0$ wt. %, or $\geq 50.0$ wt. %, or $\geq 75.0$ wt. %, or $\geq 90.0$ wt. %, or $\geq 99.0$ wt. %. For example, the first mixture can comprise $\geq 1.0$ wt. % of $C_{1+}$ alkane, based on the weight of the first mixture, such as $\geq 25.0$ wt. %, or $\geq 50.0$ wt. %, or $\geq 75.0$ wt. %, or $\geq 90.0$ wt. %, or $\geq 99.0$ wt. %. The first mixture can comprise methane, e.g., $\geq 1.0$ wt. % of methane, based on the weight of the first mixture, such as $\geq 25.0$ wt. %, or $\geq 50.0$ wt. %, or $\geq 75.0$ wt. %, or $\geq 90.0$ wt. %, or $\geq 99.0$ wt. %. Optionally, the first mixture comprises diluent, e.g., one or more of nitrogen, helium, argon, etc.

One or more electrochemical cells is utilized for converting at least a portion of the first mixture to a second mixture comprising $C_{2+}$ unsaturates. The remainder of the second mixture can be molecular hydrogen and/or ethane, for example. In certain aspects, $\geq 0.1$ wt. % of the first mixture's hydrocarbon is converted to $C_{2+}$ unsaturates of the second mixture, particularly to $C_{2+}$ olefin, e.g., $\geq 1.0$ wt. %, such as $\geq 10.0$ wt. %. In particular aspects, the first mixture comprises methane and the second mixture comprises ethylene, e.g., the first mixture comprises $\geq 90.0$ wt. % methane, such as ≥99.0 wt. % methane, and (ii) the second mixture comprises ≥90.0 wt. % ethylene, such as ≥99.0 wt. % ethylene.

The term "$C_n$" hydrocarbon wherein n is a positive integer, e.g., 1, 2, 3, 4, or 5, means hydrocarbon having n carbon atom(s) per molecule. The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n. The term "$C_{n+}$" hydrocarbon wherein n is a positive integer, e.g., 1, 2, 3, 4, or 5, means hydrocarbon having at least n carbon atom(s) per molecule. The term "alkane" means substantially saturated compounds containing hydrogen and carbon only, e.g., those containing ≤1% (molar basis) of unsaturated carbon atoms. The term alkane encompasses $C_1$ to $C_5$ linear, iso, and cyclo alkanes. The term "unsaturate" means a $C_n$ hydrocarbon containing at least one carbon atom directly bound to another carbon atom by a double or triple bond. The term "Periodic Table" means the Periodic Chart of the Elements, as it appears on the inside cover of The Merck Index, Twelfth Edition, Merck & Co., Inc., 1996.

Figure 1A:
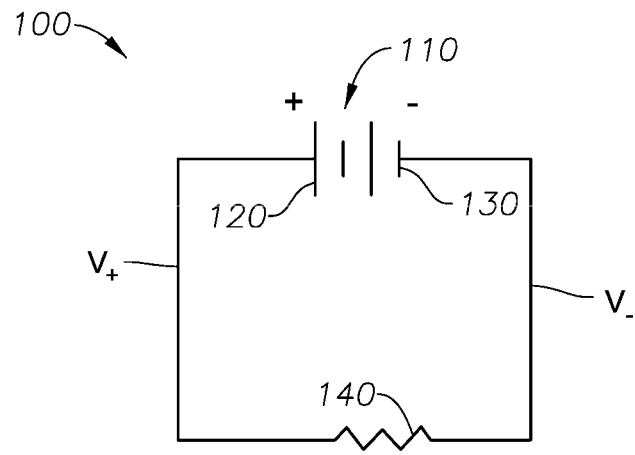
FIG. 1a schematically illustrates a circuit 100 for applying an electric potential and establishing an electric potential difference.

For the purpose of this description and appended claims, electric currents are defined in the conventional way: the direction of electric current is the direction in which positive charges move. The term "electric potential" is defined in terms of electric current flow: in traversing a resistor, for example, electric current flows from a high (more positive) electric potential to a lower (less positive, zero, or negative) electric potential. Referring to the electric circuit 100 of FIG. 1a, a source of electricity 110, e.g., a primary battery, has a positive (+) terminal 120 and negative (−) terminal 130 as shown. A device 140 (shown as a linear device, a resistor, by way of example) is connected between the positive and negative terminals. The electric potential $V_+$ is greater than electric potential $V_-$. Although $V_-$ can be referenced to an electric potential of zero volts, this is not required. For example, a bias voltage (positive or negative) can be applied to the cell, e.g., to the cell's negative terminal. An electric current is observed to flow from terminal 120 through resistor 140, to terminal 130. An electromotive force ("EMF") is the electric potential (energy) per unit positive charge gained by a positive unit charge traversing source 110. Consequently, the electric potential at the positive terminal $V_+$ of source 110 is higher (more positive) than the potential at the negative terminal, $V_-$.

Figure 1B:
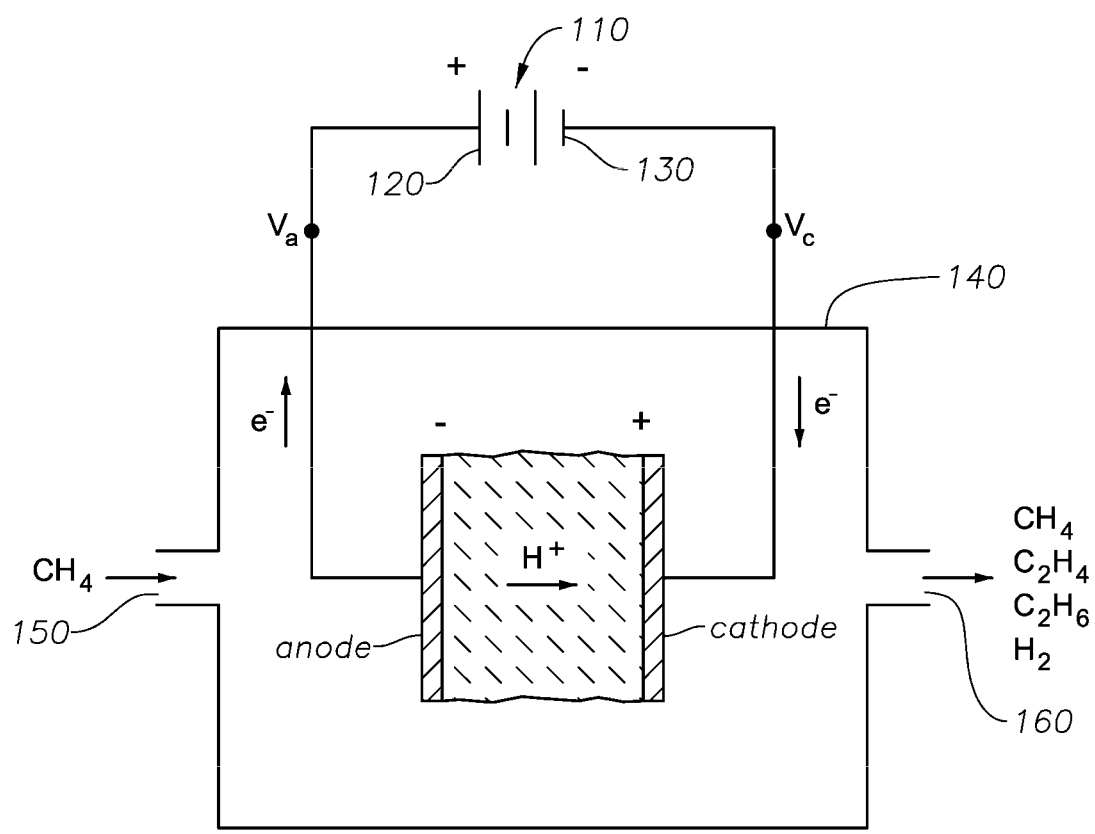
FIG. 1b schematically illustrates a circuit for applying an electric potential to an electrochemical cell to establish an electric potential difference across the cell.

The term "applying an electric potential to the cell" means electrically connecting the positive terminal 120 of source 110 to the negative terminal of an electrochemical cell, and providing an electrical return path for electric current flow from the cell's positive terminal to the source's negative terminal 130. Referring to FIG. 1b, device 140 is represented now by an electrochemical cell, which can be a linear or non-linear device depending on how it is operated. The electrochemical cell comprises an anode (negative electrode), a cathode (positive electrode), and a non-porous membrane located between the cell's anode and cathode. The cell's negative terminal (the cell's anode, from which electrons leave the cell) has an electric potential of $V_a$. The cell's positive terminal (the cell's cathode, toward which electrons enter the cell) has an electric potential of $V_c$. Electron movement is in the opposite direction of electric current flow, as shown in the figure. A first mixture comprising ≥90.0 wt. % methane based on the weight of the first mixture enters cell 140 from the left. At least a portion of the methane contacting the cell's anode is converted to $CH_2$ fragments and hydrogen ions. At least a portion of the hydrogen ions traverse the cell's membrane and combine at the cathode to form molecular hydrogen. A second mixture comprising at least a portion of (i) the molecular hydrogen, (ii) ethane and ethylene produced from $CH_2$ fragments, and (iii) unreacted methane is conducted away from the right hand side of the cell. In certain aspects, not shown, the cell is configured to prevent the flow of the first mixture from the inlet to the outlet. For example, sealing means, such as one or more o-rings, can be utilized for partitioning the cell into an anode chamber and a cathode chamber, wherein (i) the anode chamber comprises the cell's anode and a first opening 150 and (ii) the cathode chamber comprises the cell's cathode and a second opening 160. In these aspects, (i) molecular hydrogen can be removed from the cathode chamber via opening 160 and (ii) ethylene, ethane, and unreacted methane can be removed from the anode chamber via opening 150. Although FIG. 1b depicts an electrochemical cell for converting methane to molecular hydrogen and $C_2$ hydrocarbons, the invention is not limited thereto. The Figure and its description are not meant to foreclose other aspects within the broader scope of the invention, e.g., aspects where an oxygen-containing fluid (e.g., one or more oxidants, such as air, molecular oxygen, etc.) are reacted with hydrogen ions at the cell's cathode to produce water.

An electrochemical cell in chemical and thermal equilibrium in an "open circuit" configuration (electricity source 110 disconnected) generally has a characteristic electric potential difference between the cell's positive and negative terminals (the "cell potential"), which depends, e.g., on the electrode materials, reactants, products, flow rates, temperature, pressure, etc. An electric potential difference $V_i$ across a cell (equal to $V_a-V_c$) in chemical and thermal equilibrium can be increased or decreased to establish a new electric potential difference $V_f$ by applying an electric potential from electricity source 110 as shown in FIG. 1b. The invention can be practiced even when the electrical behavior of cell 140 is non-ohmic, e.g., whether cell 140 operates as a linear device, a non-linear device, or some combination thereof. The electric potential difference across a cell ($V_a-V_c$), can be measured using conventional means. For example, when source 110 produces direct current, a D.C. voltmeter can be used. When source 110 produces alternating current, $V_a-V_c$ can be measured using an oscilloscope for example.

A substantially-constant electric potential can be applied to the cell to establish the specified electric potential differences across the cell ($V_1$, $V_2$, etc.). Alternatively, the electric potential applied to the cell varies in time. For example, source having a periodic or non-periodic voltage variation can be utilized, such as an alternating current source. Example of non-constant electric potential differences across the cell which can result from applying a time-varying electric potential to the cell are shown in FIG. 1c.

Figure 1C:
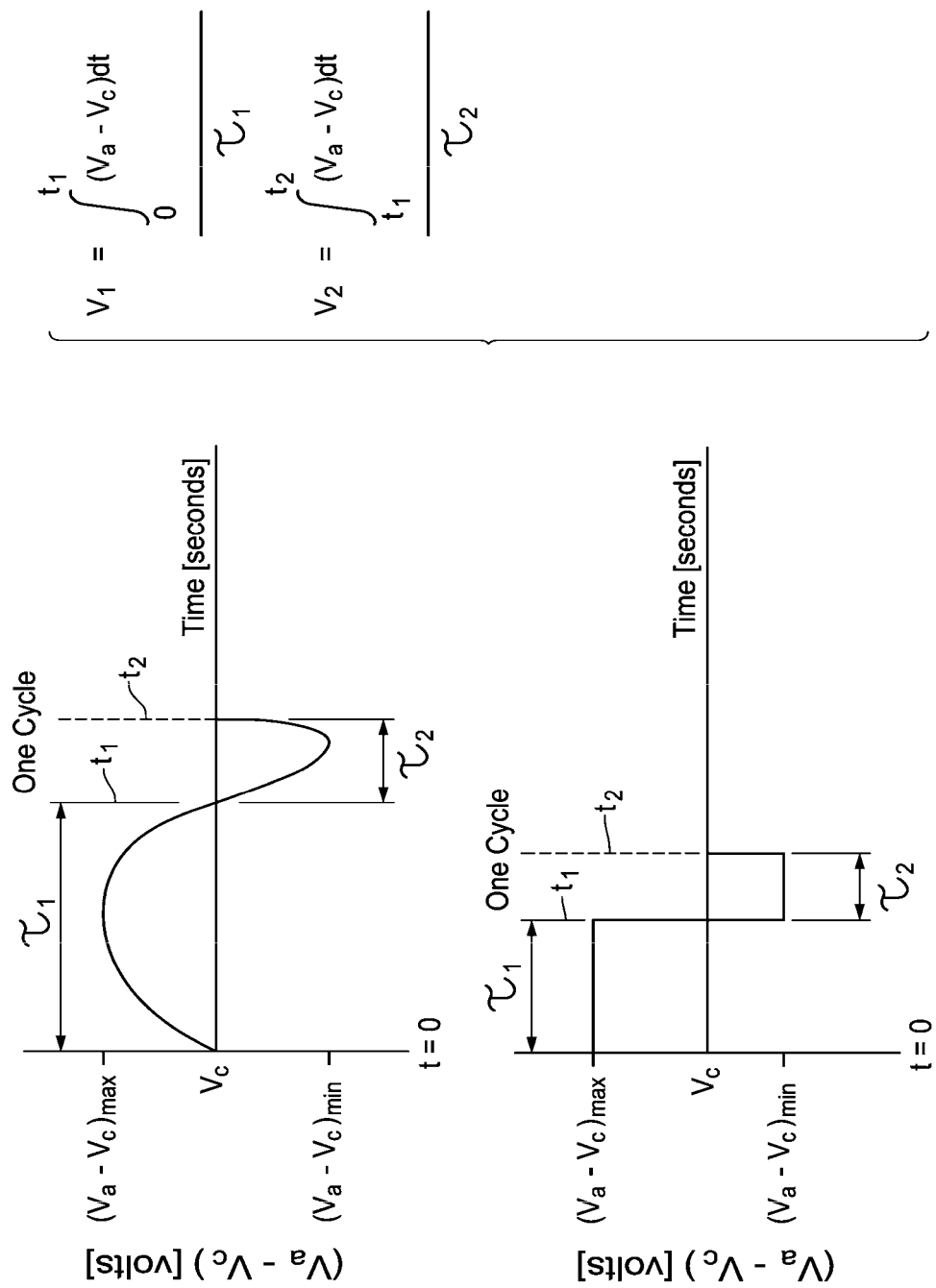
FIG. 1c schematically shows examples of electric potential waveforms that may be applied to the cell.

When the electric potential applied to the cell is not substantially constant, average values for the electric potential differences across the cell ($V_1$, $V_2$, etc.) can be defined as shown in FIG. 1c. The baseline is referenced to the electric potential of the cell's positive electrode, $V_c$, which can include an optional bias. $V_1$ is equal to the time-average value of ($V_a-V_c$) over interval $\tau_1$, and $V_2$ is equal to the time-average value of ($V_a-V_c$) over interval $\tau_2$. Average values for $V_3$, $V_4$, etc., over corresponding intervals $\tau_3$, $\tau_4$, etc., can be determined in the same way.

FIG. 1c illustrates how to do this when the applied electric potential results in establishing an electric potential difference across the cell having smoothly-varying and abruptly-changing waveforms. Average electric potential differences across the cell resulting from applying other waveform shapes to the cell (including non-periodic waveforms) can be obtained using conventional Fourier analysis, for example, such as those involving a convolution of a plurality of individual sinusoidal waveforms. Applied electric potentials can be obtained from conventional sources of electricity, such as one or more batteries, D.C. power supplies, A.C. power supplies, etc. Generators of radio frequency waves and microwaves (such as one or more transmitters) can be utilized for applying the electric potential, e.g., when at least one of $\tau_1$ and/or $\tau_2$ is $\leq 1 \times 10^{-3}$ seconds. Circuit efficiency is improved when the source of electricity has an internal impedance that is substantially the same as that of the electrochemical cell. As an example, suitable electricity sources include those capable of applying an electric potential in the range of −100 volts to 100 volts and having an internal impedance ≤1000 Ohms, such as those capable of applying an electric potential in the range of +20 volts to −20 volts, or +10 volts to −10 volts, or 0 volts to 10 volts; and having an internal impedance ≤100 ohms, e.g., ≤10 ohms.

Control means can be utilized for maintaining the desired electric potential difference across the cell at the desired value or values for the desired time period. The control means can include one or more data processors interfaced (i) with one or more voltage sensing means (e.g., a voltmeter, analog-to-digital converter, etc.) and (ii) one or more means for applying an electric potential to the cell (e.g., one or more A.C. or D.C. power supplies, batteries, etc.). For example, one or more digital or analog computers can be utilized for acquiring data from a voltmeter, the voltmeter being configured to measure the electric potential difference across the cell (e.g., $V_a - V_b$). The computer can be configured to automatically provide a correction signal to the power supply when the electric potential difference across the cell differs from the desired value. The power supply is configured to respond to the correction signal by increasing or decreasing the applied electric potential to the cell until the desired value is attained. Conventional data processors, voltage sensing means, power supplies, and interfaces/interconnections can be used to do this, but the invention is not limited thereto.

An electric potential difference across the cell can be established for a first time interval $\tau_1$ such as by applying an electric potential to the cell. More particularly, the duration of the first time interval, $\tau_1$, can be selected to be a time interval approximating the time needed to form $C_2H_4$ species at the first electrode. Duration $\tau_1$ may be approximated by a number of methods known in the art, e.g., by calculating the ratio of the moles $CH_x$ per square cm of electrode surface to the moles of $CH_2$ entering the cell for conversion as determined by the space velocity (e.g., the weight hourly space velocity, "WHSV") of the $CH_4$ entering the cell (moles/cm·sec.), which can as shown in equation (1):

$$CH_2 \sim (\text{methane feedspace velocity}) \cdot (\% \text{ conversion/pass}) \cdot (\text{electrode surface area})^{-1.} \quad (1)$$

The moles of $CH_x$ per square cm of electrode surface can be estimated according to equation (2):

$$CH_x \sim (\text{gram-atoms/cm}^2 \text{ of catalyst}) \cdot (CH_x \text{ coverage/catalyst site}). \quad (2)$$

By way of example, the time needed to form $C_2H_4$ species at an electrode having a surface area of 100 m$^2$/gram, a platinum coverage of 50% of the surface area, and a methane feed WHSV of 0.5 hr$^{-1}$, assuming a conversion of 25% per pass, and a $CH_x$ coverage moles/catalyst site of 0.45 results in an estimated value for first time interval, $\tau_1$, of 0.1 seconds.

A minimum value for the first time interval, $\tau_{1min}$, which corresponds to the minimum time needed for two $CH_2$ molecules to combine to form $C_2H_4$, can be estimated using the formula:

$$\tau_{min} = \frac{l_{min}}{v_{rms}}, \quad (3)$$

where $l_{min}$ is the minimum mean free path and $v_{rms}$ is the root mean square velocity of $CH_2$ fragments in the first electrode chamber under specified conditions of temperature and pressure. The parameter $v_{rms}$ can be estimated from the equipartition theorem:

$$v_{rms} = \sqrt{\frac{3KT}{m}}, \quad (4)$$

where m is the mass of a $CH_2$ fragment ($2.33 \times 10^{-23}$ g), K is the Boltzmann constant, and T is the temperature of the first electrode chamber in ° Kelvin (° K). For a temperature of 200° C. (473° K), $$v_{rms} = 9.23 \times 10^4 \frac{cm^2}{sec}. \quad (5)$$

The parameter $l_{min}$ can be estimated from the equation:

$$l_{min} = \frac{1}{n\sigma_{max}\sqrt{2}}, \quad (6)$$

where $\sigma_{max}$ is a $CH_2$ fragment's maximum cross sectional area and n is the number of $CH_2$ fragments per cm$^3$. The parameter $\sigma_{max}$ can be estimated using the formula:

$$\sigma_{max} = \pi d^2, \quad (7)$$

where d is twice the length of a C—H bond in cm. For a $CH_2$ fragment, $\sigma_{max}$ is approximately $1.41 \times 10^{-15}$ cm$^2$.

The parameter n can be estimated from the equation of state:

$$n = \frac{P}{KT}, \quad (8)$$

where P is the first electrode chamber pressure.

At a temperature of 200° C. (473° K) and a pressure of 1.0 atmosphere (10$^6$ dynes/cm$^2$), n is approximately $1.5 \times 10^{17}$ $CH_2$ molecules per cm$^3$, $l_{min}$ is approximately $3.35 \times 10^{-5}$ cm, and $\tau_{1min}$ is approximately $3.63 \times 10^{-10}$ sec., i.e., the estimated value of the minimum time needed for two $CH_2$ fragments to interact and form $C_2H_4$ is on the order of $1.0 \times 10^{-10}$ sec.

The maximum value of the first time interval, $\tau_{1max}$, is preferably on the order of the time, $\tau_c$, which is the time needed to successively oxidize methane in the first electrode chamber to coke. Thus, preferably $\tau_{1max} \leq 10.0 \cdot \tau_c$, e.g., $\tau_{1max} \leq 1.0 \cdot \tau_c$, such as $\tau_1 \leq 0.1 \cdot \tau_c$. In particular aspects, $\tau_1 \leq \tau_{CH}$, wherein $\tau_{CH}$ is a time needed to produce on the first electrode $1.0 \times 10^{-9}$ mole cm$^{-2}$ of carbon atoms from CH fragments during each application of the electric potential difference across the cell for a first time interval $\tau_1$.

Thus, in some aspects, first time interval, $\tau_1$, may be from $1.0 \times 10^{-10}$ to 10.0 sec. The lower limit on the first time interval, $\tau_1$, may be selected from values of e.g., $1.0 \times 10^{-10}$ sec., $1.0 \times 10^{-9}$ sec., $1.0 \times 10^{-8}$ sec., $1.0 \times 10^{-7}$ sec., $1.0 \times 10^{-6}$ sec., $1.0 \times 10^{-5}$ sec., $1.0 \times 10^{-4}$ sec., $1.0 \times 10^{-3}$ or $1.0 \times 10^{-2}$ sec. The upper limit on the first time interval, $\tau_1$, may be selected from values of e.g., 10.0 sec., 5.0 sec., 2.5 sec., 1.0 sec., 0.5 sec., 0.25 sec., 0.10 sec., 0.05 sec., 0.02 sec., 0.01 sec., $1.0 \times 10^{-3}$ sec., $1.0 \times 10^{-4}$ sec., $1.0 \times 10^{-5}$ sec., $1.0 \times 10^{-6}$ sec., $1.0 \times 10^{-2}$ sec., $1.0 \times 10^{-8}$ sec., $1.0 \times 10^{-9}$ sec. In particular embodiments, the first time interval, $\tau_1$, may be $1.0 \times 10^{-10}$ to 1.0 sec., $1.0 \times 10^{-10}$ to 0.1 sec., or $1.0 \times 10^{-10}$ to 0.01 sec., $1.0 \times 10^{-10}$ to $1.0 \times 10^{-8}$ sec., or $1.0 \times 10^{-9}$ to $1.0 \times 10^{-8}$ sec. Other exemplary ranges for the first time interval, $\tau_1$, include 0.05 sec. to 0.25 sec., 0.01 to 0.2 sec., or 0.001 to 0.1 sec. In other embodiments the first time interval, $\tau_1$, may be $1.0 \times 10^{-10}$ to $1.0 \times 10^{-6}$ sec.

Optionally, the duration of the first interval is regulated so that it is less than the time needed to form an appreciable amount of carbon at the first electrode. Optionally, the duration of the second time interval is regulated so that an appreciable amount of ethylene can form from the interaction of the CH$_2$ fragments, and so that carbon that has formed at the first electrode can react with H$^+$ and e$^-$ to restore CH$_x$ fragments on the first electrode surface. Preferably the duration of the first and second intervals are selected and regulated so that two or more of these desired effects can occur.

The temperature and pressure of the first mixture when an electric potential difference is established across the cell during a first time interval is not critical. In particular embodiments, however, improved results may be achieved where the temperature of the first mixture is from 100° C. to 500° C. (e.g., $1.0 \times 10^{2}$° C. to $5.0 \times 10^{2}$° C.). In some embodiments, lower limit on the range of temperature of the first mixture during that application of the electric potential difference for the first time interval may be 100° C., 125° C., 150° C., 175° C., 200° C., 225° C., 250° C., 300° C., 350° C., 375° C., 400° C., 450° C., 475° C., 480° C., 490° C., or 495° C. The upper limits on the range of temperatures of the first mixture may be 125° C., 150° C., 175° C., 200° C., 225° C., 250° C., 300° C., 350° C., 375° C., 400° C., 450° C., 475° C., 480° C., 490° C., 495° C., or 500° C. Any upper limit may be matched with any lower limit; e.g., 100° C. to 300° C., 200° C. to 450° C. or 180° C. to 225° C. A stream at such temperature may be at a pressure of 0.1 bar to 100.0 bar, preferably 1.0 to 50.0 bar, 5.0 to 50.0 bar, 1.0 to 25.0 bar, 5.0 to 25.0 bar, 1.0 to 20.0 bar, 5.0 to 20.0 bar, 1.0 to 15.0 bar, 5.0 to 15.0 bar, 1.0 to 10.0 bar, 5.0 to 10.0 bar 1.0 to 5.0 bar, or 1.0 to 2.5 bar. Such temperatures and pressures typically refer to the temperature and pressure of the first electrode chamber.

In particular aspects, the electric potential difference established across the cell during the first time interval, $\tau_1$, is selected so that the current density, $I_1$ through the membrane during the first time interval, $\tau_1$, achieves a value of 1.0 mA cm$^{-2}$ to 100.0 mA cm$^{-2}$. The lower limit on the current density $I_1$ may be 1.0 mA cm$^{-2}$, 2.0 mA cm$^{-2}$, 5.0 mA cm$^{-2}$, 7.5 mA cm$^{-2}$, 10.0 mA cm$^{-2}$, 15.0 mA cm$^{-2}$, 20.0 mA cm$^{-2}$, 25.0 mA cm$^{-2}$, 30.0 mA cm$^{-2}$, 40.0 mA cm$^{-2}$, 50.0 mA cm$^{-2}$, 60.0 mA cm$^{-2}$, 70.0 mA cm$^{-2}$, 80.0 mA cm$^{-2}$, 85.0 mA cm$^{-2}$, 90.0 mA cm$^{-2}$, 95.0 mA cm$^{-2}$, or 99.0 mA cm$^{-2}$. An upper limit on the range of the current density $I_1$ may be 2.0 mA cm$^{-2}$, 5.0 mA cm$^{-2}$, 7.5 mA cm$^{-2}$, 10.0 mA cm$^{-2}$, 15.0 mA cm$^{-2}$, 20.0 mA cm$^{-2}$, 25.0 mA cm$^{-2}$, 30.0 mA cm$^{-2}$, 40.0 mA cm$^{-2}$, 50.0 mA cm$^{-2}$, 60.0 mA cm$^{-2}$, 70.0 mA cm$^{-2}$, 80.0 mA cm$^{-2}$, 85.0 mA cm$^{-2}$, 90.0 mA cm$^{-2}$, 95.0 mA cm$^{-2}$, 99.0 mA cm$^{-2}$, or 100.0 mA cm$^{-2}$. Any upper limit may be matched with any lower limit; e.g., preferably 5.0 mA cm$^{-2}$ to 75.0 mA cm$^{-2}$ or 15.0 mA cm$^{-2}$ to 50.0 mA cm$^{-2}$. Such current densities may be achieved by establishing an electric potential difference across the cell that is in the range of 0.1 to 20.0 V, particularly 1.0 to 20.0 V, 0.1 to 15.0 V, 1.0 to 15.0 V, 0.1 to 10.0 V, 5.0 to 10.0 V, 1.0 to 10.0 V, 0.1 to 5.0 V, or 1.0 to 5.0 V across the cell during the first time interval, $\tau_1$.

After the cell is operated at the operating electric potential difference for the first time interval, $\tau_1$, the electric potential difference across the cell is lessened, reversed, or substantially removed for a second time interval, $\tau_2$. The second time interval, $\tau_2$, is typically is selected such that $\tau_2 \leq \tau_1$. For example, $\tau_2$ may be $0.01 \cdot \tau_1$ to $0.9 \cdot \tau_1$, $0.05 \cdot \tau_1$ to $0.8 \cdot \tau_1$, $0.1 \cdot \tau_1$ to $0.7 \cdot \tau_1$, $0.2 \cdot \tau_1$ to $0.6 \cdot \tau_1$, $0.3 \cdot \tau_1$ to $0.5 \cdot \tau_1$, particularly $\tau_2 = 0.01 \cdot \tau_1$ to $0.5 \cdot \tau_1$, $0.01 \cdot \tau_1$ to $0.25 \cdot \tau_1$, $0.01 \cdot \tau_1$ to $0.1 \cdot \tau_1$.

The electric potential difference during the second time interval is typically maintained in a range such that substantially no oxidation of CH to carbon occurs. Thus, the value of the electric potential difference across the cell during the second time interval, $V_2$, is generally less than the electric potential difference across the cell during the first time interval, $V_1$. Optionally, $V_1$ and $V_2$ are related as follows:
 (i) $V_1 > 0$, $V_2 \geq 0$, and $V_2 = A_1 \cdot V_1$, where $A_1$ is in the range of from about 0.1 to about 0.9, such as in the range of from about 0.2 to about 0.8;
 (ii) $V_1 \geq 0$ and $V_2 < 0$; or
 (iii) $V_1 < 0$, $V_2 < 0$, and $|V_2| = A_2 |V_1|$, where $A_2 \geq 1.1$, e.g., $\geq 2$, such as $\geq 10$. Optionally, $V_1 \geq 0$, and $|V_2| < |V_1|$. In certain embodiments where $V_1$ is positive, $V_2 = -1.0 \cdot V_1$ to $0.1 \cdot V_1$, or 0 to $0.1 \cdot V_1$. Alternatively, the electric potential difference may be selected to produce a second current density through the cell, $I_2$, where $I_2$ is in the range of $-10.0 \cdot I_1$ to $0.9 \cdot I_1$.

Optionally, $V_2$ and $V_3$ can be related as follows:
 (i) $V_3 > 0$, $V_2 \geq 0$, and $V_2 = A_3 \cdot V_3$, where $A_3$ is in the range of from about 0.1 to about 0.9, such as in the range of from about 0.2 to about 0.8;
 (ii) $V_3 \geq 0$ and $V_2 < 0$; or
 (iii) $V_3 < 0$, $V_{2<0}$, and $|V_2| = A_4 |V_3|$ where $A_4 \geq 1.1$, e.g., $\geq 2$, such as $\geq 10$. Optionally, $V_3 \geq 0$, and $|V_2| < |V_3|$. In certain embodiments, $V_3$ is substantially the same as $V_1$, $\tau_3$ is substantially the same as $\tau_1$, and $I_3$ is substantially the same as $I_1$.

Optionally, $V_3$ and $V_4$ are related as follows:
 (i) $V_3 > 0$, $V_4 \geq 0$, and $V_4 = A_5 \cdot V_3$, where $A_5$ is in the range of from about 0.1 to about 0.9, such as in the range of from about 0.2 to about 0.8;
 (ii) $V_3 \geq 0$ and $V_4 < 0$; or
 (iii) $V_3 < 0$, $V_4 < 0$, and $|V_4| = A_6 |V_3|$, where $A_6 \geq 1.1$, e.g., $\geq 2$, such as $\geq 10$. Optionally, $V_3 \geq 0$, and $|V_4| < |V_3|$. In certain aspects, $V_4$ is substantially the same as $V_2$, $\tau_4$ is substantially the same as $\tau_2$, and $I_4$ is substantially the same as $I_2$.

Methane can be continuously converted to C$_{2+}$ unsaturates at the first electrode without producing an appreciable amount of carbon on the first electrode. Typically, the process is operated cyclically, by applying an alternating electric potential to the cell to establish an alternating electric potential difference across the cell. The electric potential difference across the cell can be in the range of from about 0.1 rms volts to 20.0 rms volts at a frequency (in Hertz)$\geq (2\cdot\pi\cdot\tau_{min})^{-1}$. The shape of the electric potential difference wave-form can be, e.g., one or more of sinusoidal, trapezoidal, rectangular, and combinations thereof. Symmetric waveforms ($V_1$ substantially the same as $V_2$, $\tau_1$ substantially the same as $\tau_2$) can be utilized. Optionally, the waveform is modulated by, e.g., a linear or non-linear function, in amplitude, frequency, or a combination thereof. Optionally, the waveform is symmetric about an axis that is substantially equal to zero volts.

Optionally, at least a portion of the $C_{2+}$ unsaturates may be conducted away from the first electrode, particularly at a rate $\geq 1.0\times 10^{-7}$ mole min$^{-1}$ cm$^{-2}$, preferably $1.0\times 10^{-7}$ mole min$^{-1}$ cm$^{-2}$ to $1.0\times 10^{-5}$ mole min$^{-1}$ cm$^{-2}$. In particular aspects, the rate is $5.0\times 10^{-6}$ mole min$^{-1}$ cm$^{-2}$ to $5.0\times 10^{-5}$ mole min$^{-1}$ cm$^{-2}$ or $1.0\times 10^{-6}$ mole min$^{-1}$ cm$^{-2}$ to $0.5\times 10^{-6}$ mole min$^{-1}$ cm$^{-2}$. The $C_{2+}$ unsaturates may be conducted away either continuously or periodically. In particular embodiments, the $C_{2+}$ unsaturates are conducted away periodically for $\geq 100.0$ minutes, preferably 100.0 to 1000.0 minutes or more. In some aspects, the lower limit on the period that the $C_{2+}$ unsaturates may be conducted away from the first electrode may be 150.0 mins., 200.0 mins., 250.0 mins., 300.0 mins., 350.0 mins., 400.0 mins., 450.0 mins., 500.0 mins., 550.0 mins., 600.0 mins., 650.0 mins., 700.0 mins., 750.0 mins., 800.0 mins., 850.0 mins., 900.0 mins., or 950.0 mins. Such lower limit may be coupled with an upper limit on the period of 200.0 mins., 250.0 mins., 300.0 mins., 350.0 mins., 400.0 mins., 450.0 mins., 500.0 mins., 550.0 mins., 600.0 mins., 650.0 mins., 700.0 mins., 750.0 mins., 800.0 mins., 850.0 mins., 900.0 mins., 950.0 mins., 1000.0 mins., 2000.0 mins., or 2500.0 mins. Any upper limit may be matched with any lower limit; e.g., 150.0 to 950.0 mins., 200.0 to 900.0 mins., 250.0 to 850.0 mins., 300.0 to 800.0 mins., 350.0 to 750.0 mins., 800.0 to 1000.0 mins.

Optionally, the processes described herein may also further include conducting water away from the first electrode and/or the second electrode. The water may be conducted away either continuously or periodically. In particular aspects, the water is conducted away periodically for $\geq 100.0$ minutes, preferably 100.0 to 1000.0 minutes or more. In some embodiments, the lower limit on the period water is conducted away from the first electrode may be 150.0 mins., 200.0 mins., 250.0 mins., 300.0 mins., 350.0 mins., 400.0 mins., 450.0 mins., 500.0 mins., 550.0 mins., 600.0 mins., 650.0 mins., 700.0 mins., 750.0 mins., 800.0 mins., 850.0 mins., 900.0 mins., or 950.0 mins. Such lower limit may be coupled with an upper limit on the period of 200.0 mins., 250.0 mins., 300.0 mins., 350.0 mins., 400.0 mins., 450.0 mins., 500.0 mins., 550.0 mins., 600.0 mins., 650.0 mins., 700.0 mins., 750.0 mins., 800.0 mins., 850.0 mins., 900.0 mins., 950.0 mins., 1000.0 mins., 2000.0 mins., or 2500.0 mins. Any upper limit may be matched with any lower limit; e.g., 150.0 to 950.0 mins., 200.0 to 900.0 mins., 250.0 to 850.0 mins., 300.0 to 800.0 mins., 350.0 to 750.0 mins., 800.0 to 1000.0 mins.

Optionally, aspects of the processes described herein may further include conducting an oxygen-containing mixture to the electrochemical cell's cathode when an electric potential difference $V_1$ has been established across the cell during the first time interval, $\tau_1$. The oxygen-containing mixture preferably comprises $\geq 10.0$ wt. % molecular oxygen ($O_2$), based on the weight of the oxygen-containing mixture. Optionally, the oxygen-containing mixture may be air or comprise 10.0 to 100.0 wt. % $O_2$, particularly 10.0 to 99.0 wt. % $O_2$, 20.0 to 90.0 wt. % $O_2$. The lower limit on range of $O_2$ in the oxygen-containing mixture may be 12.5 wt. %, 15.0 wt. %; 20.0 wt. %, 25.0 wt. %, 30.0 wt. %, 40.0 wt. %, 50.0 wt. %, 60.0 wt. %, 70.0 wt. %, 75.0 wt. %, 80.0 wt. %, 90.0 wt. %, 95.0 wt. %, or 99.0 wt. %. Such lower limit may be coupled with an upper limit on the $O_2$ content of 15.0 wt. %; 20.0 wt. %, 25.0 wt. %, 30.0 wt. %, 40.0 wt. %, 50.0 wt. %, 60.0 wt. %, 70.0 wt. %, 75.0 wt. %, 80.0 wt. %, 90.0 wt. %, 95.0 wt. %, 99.0 wt. %, or 100.0 wt. %. Any upper limit may be matched with any lower limit.

$C_{2+}$ unsaturates formed in aspects of the processes described herein may be further reacted by any number of suitable reaction types, e.g., oligomerization, polymerization, hydroxylation, and/or hydrogenation.

Figure 5:
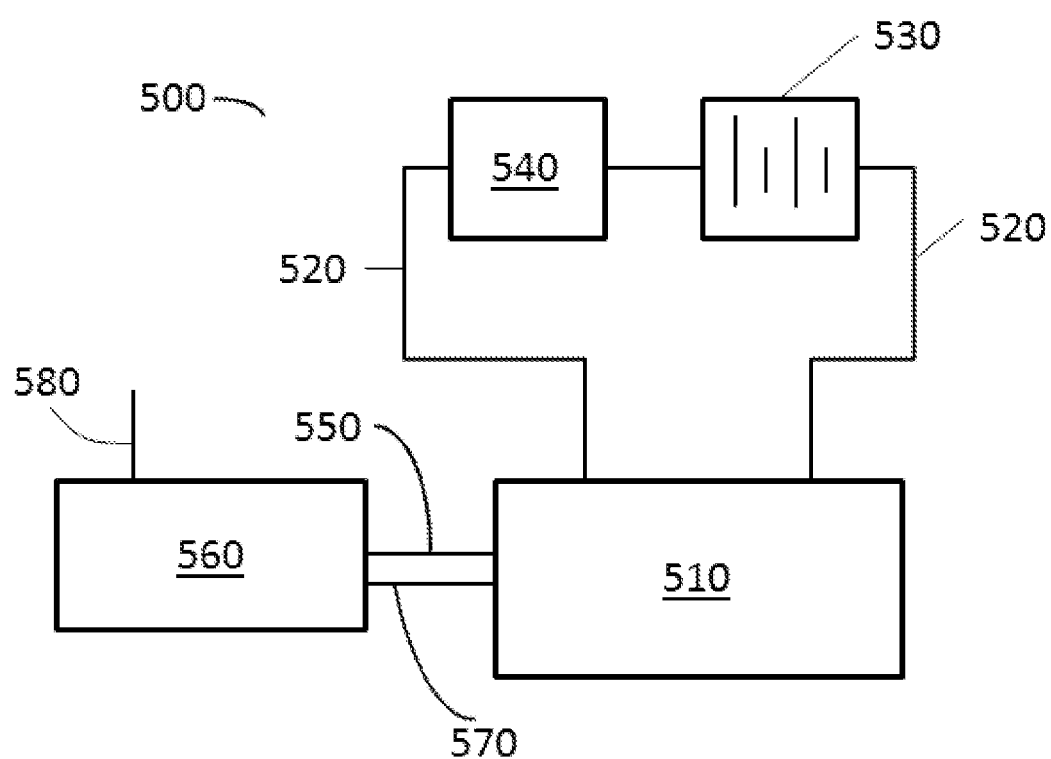
FIG. 5 schematically illustrates an apparatus for the electrocatalytic conversion of hydrocarbons according to the invention.

The configuration of the electrocatalytic apparatus for the processes described above is not critical provided that it is capable of converting at least a portion of a methane-containing stream to $C_2^+$ unsaturates. FIG. 5 illustrates a schematic representation of an apparatus 500 for the electrocatalytic conversion of hydrocarbons according to an embodiment of the invention. Apparatus 500 includes an electrochemical cell 510. The electrochemical cell 510 is connected via electrical contacts 520 to a source of electricity 530 capable of applying an electric potential to the cell sufficient for establishing an electric potential difference across the cell. The electric potential difference established across the cell causes an electric current to flow through the cell, which current and electric potential difference activate the formation of $CH_3$ fragments from methane. The electric potential applied to the cell (and the current flowing through the cell) can be regulated by providing electricity source 530 with voltage regulation means 540 (e.g., a voltage regulator, such as a conventional three-terminal regulator). FIG. 5 shows voltage regulator 540 connected in series with electricity source 530, but this is not required, and in certain embodiments one or more voltage regulators are connected with electricity source 530 in series, parallel, or a with a combination of series and parallel connections. In particular embodiments, voltage regulator 530 is integral with the power supply 530. The voltage regulator 540 is configured to apply a desired electric potential to cell 510 to produce the desired electric potential difference across the cell (and/or a desired electric current through the cell 510) for a first time interval of duration $\tau_1$. The voltage regulator 540 is configured to, after the time $\tau_1$, to lessen, reverse, or substantially remove the supply of power to the cell 510 for a second time interval of duration $\tau_2$. Current regulation (not shown) can be used with or as an alternative to voltage regulation.

Optionally, apparatus 500 may also include conduit 550 fluidly connected to a separation unit 560 for separating $C_{2+}$ compounds formed in the cell 510 from reactant gases. Apparatus 500 may also include recycle conduit 570 to return unreacted reactant gases to the cell 510 and conduit 580 configured to send $C_{2+}$ compounds, particularly $C_2^+$ unsaturates for further processing, e.g., hydrogenation, oligomerization, polymerization hydroxylation, etc.

Figure 6:
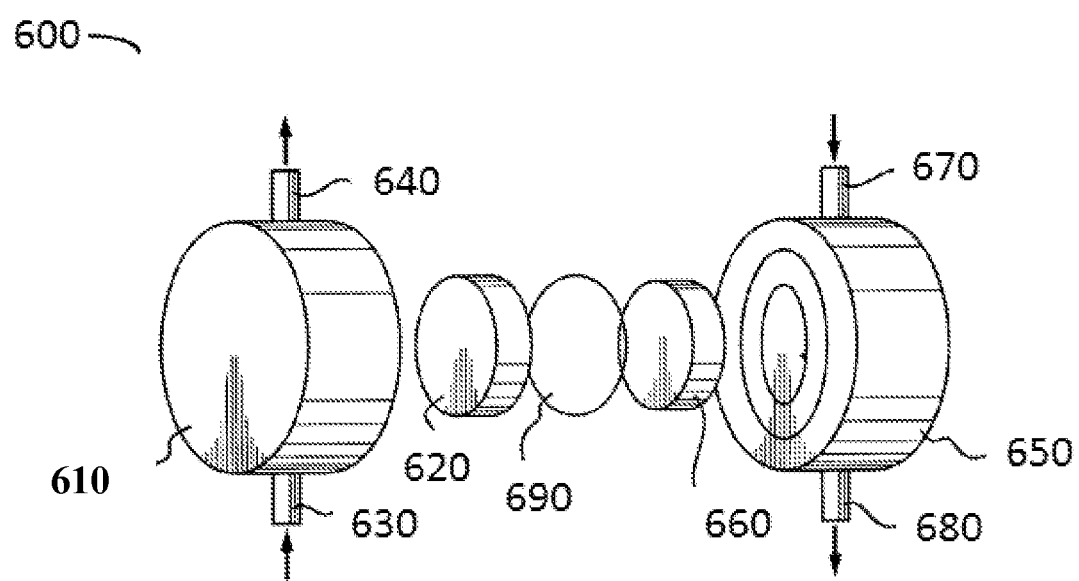
FIG. 6 schematically illustrates an electrochemical cell for use in the electrocatalytic conversion of hydrocarbons according to the invention.

FIG. 6 illustrates an aspect of the electrochemical cell 510 of FIG. 5. Electrochemical cell 600 includes first electrode chamber 610, e.g., anode chamber, having a first electrode, e.g., an anode, 620. The first electrode chamber 610 is configured with means to receive the first mixture comprising $\geq 1.0$ wt. % methane, ethane, or methanol in contact with the electrode (based on the weight of the first mixture) via inlet 630. First electrode chamber 610 may also include one or more outlets 640 including means for withdrawing higher hydrocarbons from the first electrode chamber 610. The electrochemical cell 600 also includes a second electrode chamber, e.g., a cathode chamber, 650 having a second electrode, e.g., a cathode, 660 therein. The second electrode chamber 650 is optionally configured to receive an oxygen-containing mixture comprising ≥10.0 wt. % molecular oxygen (based on the weight of the oxygen-containing mixture) through inlet 670. Second electrode chamber 650 typically also includes means for withdrawing hydrogen and/or water therefrom via outlet 680. A membrane 690 is provided between the first electrode chamber 610 and the second electrode chamber 650. The membrane 690 is configured to provide diffusive and electrical contact between the first and second electrodes. Apparatus 500 may also optionally include means for removing heat from the second electrode chamber 650. Such means may include, e.g., a heat exchanger or a sweep gas supply. If desired, sealing means (not shown) such as o-rings can be utilized for substantially preventing the flow (or diffusion) of reactants and/or products between the electrodes and the inner surfaces of the electrode chambers.

Figure 7:
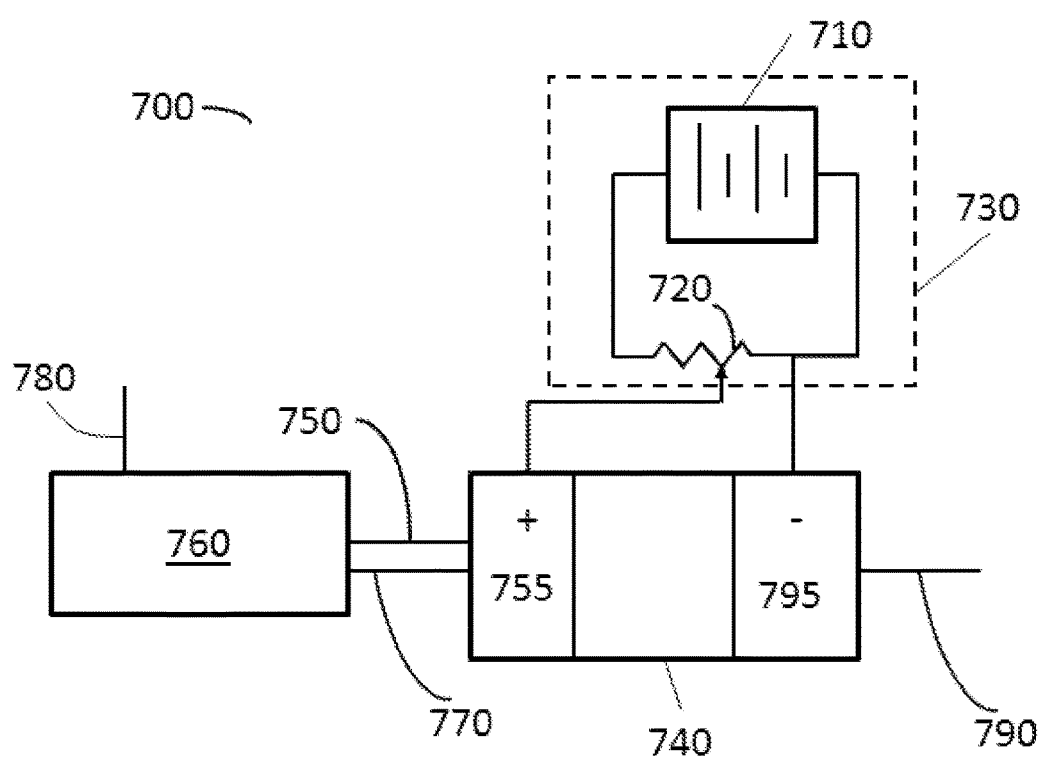
FIG. 7 schematically illustrates an alternative apparatus for the electrochemical conversion of hydrocarbons according to the invention.

FIG. 7 schematically illustrates an alternative apparatus 700 for the electrocatalytic conversion of hydrocarbons according to an embodiment of the invention. In apparatus 700, power supply 710 and resistor 720 form a potentiometer 730. Potentiometer 730 is electrically connected to electrochemical cell 740, which may be of the type illustrated in FIG. 6. In such a configuration, potentiometer 730 can be adjusted to apply an electric potential to the cell in order to establish an electric potential difference across cell 740. Thus, potentiometer 730 may be adjusted to establish a control (e.g., automatically control) on electric potential difference across the cell ($V_1$) and an amount of electric current flowing through the cell ($I_1$) for the desired first time interval duration $\tau_1$ and thereafter lessen, reverse, or substantially remove the electric potential applied to cell 740 in order to establish a second electric potential difference across the cell ($V_2$) and a second amount of electric current flowing through the cell ($I_2$) for a desired second time interval $\tau_2$. Apparatus 700 may also include conduit 750 fluidly connecting the anode chamber 755 to separation unit 760 for separating $C_{2+}$ compounds formed in the cell 740. Separation unit 760 is configured to return unreacted reactant gases to the cell 740 via recycle conduit 770. Conduit 780 configured to send $C_{2+}$ compounds, particularly $C_{2+}$ unsaturates for further processing, e.g., hydrogenation, oligomerization, polymerization hydroxylation, etc. Apparatus 700 may also include an oxygen-containing-gas supply 790 in fluid communication with the cathode chamber 795 of cell 740. Aspects of the invention illustrated in FIG. 7 are not limited to those utilizing passive components (e.g., battery variable resistor) as shown in the figure. Active components and combinations of active and passive components for providing the indicated potentiometric functionality can be used instead.

The first electrode typically comprises at least one metal selected from Group VIII of the Periodic Table. For example, the second electrode may comprise ≥1.0 wt. % of at least one noble metal based on the weight of the first electrode. The first electrode may include compressed carbon powder loaded with noble metal, carbon cloths supporting noble metal, nickel mesh impregnated with noble metal, etc. Among particularly useful noble metals, include Ag, Pt, Pd, Ru, etc. The first electrode may be a particular surface of a noble metal electrode, e.g., Ni(111), Pd(111), and Pt(111). In particular embodiments, the first electrode is the anode.

The second electrode typically comprises at least one metal selected from Group VIII of the Periodic Table. For example, the second electrode may comprise ≥1.0 wt. % of at least one noble metal based on the weight of the second electrode. Like the first electrode, the second electrode may include compressed carbon powder loaded with noble metal, carbon cloths supporting noble metal, nickel mesh impregnated with noble metal, etc. Among particularly useful noble metals, include Ag, Pt, Pd, Ru, etc. In particular embodiments, the second electrode may be a particular surface of a noble metal electrode, e.g., Ni(111), Pd(111), and Pt(111). The composition and structure of the second electrode may be the same or different composition or surface than that of the first electrode. In particular embodiments, the second electrode is the cathode.

The electrochemical cell generally comprises at least one membrane, e.g., at least one non-porous membrane, located between the first and second electrode. When more than one membrane is used, the membranes can be configured as a membrane assembly located between the first and second electrodes, each membrane of the assembly being in face-to-face contact with its neighboring membrane. Although all the membranes of the membrane assembly can be of the same composition and have the same thermal and transport properties, this is not required, and in certain embodiments the membranes comprising the membrane assembly have different compositions and properties. In particular embodiments, the membrane utilized in the cell of apparatus 400 comprises solid, proton-conducting membrane separating the first electrode chamber from the second chamber, particularly a non-porous membrane. As used herein, the term "non-porous" means that the membrane is impervious to gaseous diffusion of methane into from one chamber to the other under zero cell current and up to 2 times the operational feed-gas pressure. The membrane provides diffusive and electrical contact between the first and second electrodes. Any suitable membrane may be used. Particular membranes capable of transferring the $H^+$ from the first electrode chamber, e.g., the anode chamber, to the second electrode chamber, e.g., the cathode chamber, include, but are not limited to, phosphoric acid, perfluorosulfonic acid and/or polybenzimidazole. Further details of the use of perfluorosulfonic acid and/or polybenzimidazole membranes are described in U.S. Pat. No. 6,294,068. Other membranes are ceramics, e.g., $SrCe_{0.95}Yb_{0.05}O_3$ as described in *Electrochemical Methane Coupling Using Protonic Conductors*; S. Hamakawa, et. al.; *J. Electrochem. Soc.*, 40(2), 459-463 (1993).

Although the invention can utilize one electrochemical cell, it is not limited thereto, and the preceding description is not meant to foreclose other embodiments within the broader scope of the invention, such as those utilizing a plurality of electrochemical cells connected in series, parallel, or series-parallel.

A representative electrochemical cell can comprise:
(i) a first electrode chamber, the first electrode chamber, comprising a first electrode, the first electrode chamber configured to receive a first mixture comprising ≥1.0 wt. % hydrocarbon based on the weight of the first mixture;
(ii) a second electrode chamber comprising a second electrode, said second electrode chamber configured to receive an oxygen-containing mixture comprising ≥10.0 wt. % molecular oxygen, based on the weight of the oxygen-containing mixture; and
(iii) at least one non-porous membrane configured to provide diffusive and electrical contact between the first electrode and the second electrode.

The electrochemical cell can further comprise a source of electricity in electrical communication with the electrochemical cell for applying an electric potential to the cell; and a voltage regulator configured to adjust the applied electric potential to establish a first electric potential difference, $V_1$ across the electrochemical cell for a first time interval of duration $\tau_1$ and a second electric potential difference, $V_2$ across the electrochemical cell for a second time interval of duration $\tau_2$. Optionally, $\tau_2 \leq \tau_1$ and $V_2$ is more negative or less positive than $V_1$.

All patents, test procedures, and other documents cited herein, including priority documents, are fully incorporated by reference to the extent such disclosure is not inconsistent with this invention and for all jurisdictions in which such incorporation is permitted. Should the disclosure of any of the patents and/or publications that are incorporated herein by reference conflict with the present specification to the extent that it might render a term unclear, the present specification shall take precedence.

As is apparent from the foregoing general description and the specific embodiments, while forms of the invention have been illustrated and described, various modifications can be made without departing from the spirit and scope of the invention. Accordingly, it is not intended that the invention be limited thereby. Many variations will suggest themselves to those skilled in this art in light of the above detailed description. All such variations are within the full intended scope of the appended claims. Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

What is claimed is:

1. A method of reducing coke formation in the electrochemical production of $C_{2+}$ unsaturates in an electrochemical cell comprising a first electrode, a second electrode, and at least one membrane situated between the first and second electrodes, the method comprising:
   (a) providing to the first electrode of the electrochemical cell a first mixture comprising $\geq 1.0$ wt. % methane based on the weight of the first mixture;
   (b) applying an electric potential difference to the electrochemical cell to establish a first electric potential $V_1$ across the electrochemical cell sufficient to convert at least a portion of the methane during a first time interval of duration $\tau_1$, wherein (i) the conversion is carried out substantially without oxidant, and (ii) $\tau_1$ is in the range of from $1 \times 10^{-10}$ sec. to 1.0 sec.;
   (c) establishing a second electric potential difference $V_2$ across the cell during a second time interval of duration $\tau_2$, wherein $\tau_2 \leq \tau_1$; and
   (d) repeating steps (b) and (c), and at least during step (c) producing $C_{2+}$ unsaturates.

2. The method of claim 1, further comprising conducting at least a portion of the $C_{2+}$ unsaturates away from the first electrode at a rate $\geq 1.0 \times 10^{-7}$ mole min.$^{-1}$cm$^{-2}$ for $\geq 100.0$ minutes.

3. The method of claim 1, wherein during step (c) the first mixture is exposed to a temperature in the range of from 100° C. to 500° C. at a pressure in the range of from 0.1 bar to 100.0 bar.

4. The method of claim 1, wherein the first electrode and/or the second electrode comprises $\geq 1.0$ wt. % of at least one noble metal.

5. The method of claim 1, wherein the current density through the membrane during step (c) achieves a value in the range of from 1.0 mA cm$^{-2}$ to 100.0 mA cm$^{-2}$.

6. The method of claim 1, wherein $V_1$ achieves a value in the range of from 0.1 Volts to 20 Volts during step (b).

7. The method of claim 1, wherein $V_1$ and $V_2$ satisfy at least one of: (i) $V_1 > 0$, $V_2 \geq 0$, and $V_2 = A_1 \cdot V_1$, wherein $A_1$ is in the range of from about 0.00 to about 0.99; (ii) $V_1 \geq 0$ and $V_2 < 0$; (iii) $V_1 < 0$, $V_2 < 0$, and $|V_2| = A_2 |V_1|$, wherein $A_2 \geq 1.01$; (iv) $V_2$ is more negative or less positive than $V_1$; or (v) $V_1 \geq 0$, and $|V_2| < |V_1|$.

8. The method of claim 1, wherein $\tau_2$ is in the range of from $0.01 \cdot \tau_1$ to $0.9 \cdot \tau_1$.

9. The method of claim 1, further comprising a step of oligomerization, polymerization, hydroxylation, or hydrogenation of at least a portion of the $C_{2+}$ unsaturates.

\* \* \* \* \*